（12） United States Patent
Alper

(10) Patent No.: US 9,402,392 B2
(45) Date of Patent: Aug. 2, 2016

(54) ADVANCED VISCOELASTIC ANTIMICROBIAL COMPOSITIONS AND METHODS

(71) Applicant: MYCELX TECHNOLOGIES CORPORATION, Duluth, GA (US)

(72) Inventor: Hal Alper, Flowery Branch, GA (US)

(73) Assignee: MyCelx Technologies Corporation, Duluth, GA (US)

(*) Notice: Subject to any disclaimer, the term of this patent is extended or adjusted under 35 U.S.C. 154(b) by 0 days.

(21) Appl. No.: 14/792,876

(22) Filed: Jul. 7, 2015

(65) Prior Publication Data

US 2015/0305330 A1    Oct. 29, 2015

Related U.S. Application Data

(63) Continuation-in-part of application No. 13/494,410, filed on Jun. 12, 2012, now Pat. No. 9,102,549, and a continuation-in-part of application No. 13/494,386, filed on Jun. 12, 2012, now abandoned.

(60) Provisional application No. 61/520,646, filed on Jun. 13, 2011.

(51) Int. Cl.
*C09D 5/14* (2006.01)
*C09D 191/00* (2006.01)
(Continued)

(52) U.S. Cl.
CPC ............... *A01N 25/34* (2013.01); *A01N 61/00* (2013.01); *C02F 1/285* (2013.01); *C02F 1/50* (2013.01); *C08F 242/00* (2013.01); *C09D 5/14* (2013.01); *C09D 191/005* (2013.01); *C02F 1/001* (2013.01); *C02F 2103/42* (2013.01); *C02F 2303/04* (2013.01); *C02F 2303/20* (2013.01); *C08L 2205/02* (2013.01); *Y02W 10/37* (2015.05)

(58) Field of Classification Search
None
See application file for complete search history.

(56) References Cited

U.S. PATENT DOCUMENTS 2,160,532 A   5/1939   Barrett et al.
2,418,920 A   4/1947   Berger et al.
(Continued)

FOREIGN PATENT DOCUMENTS

BE    859836       2/1978
WO    99/48584 A2  9/1999
(Continued)

OTHER PUBLICATIONS

D. Swern, ed. Bailey's Industrial Oil and Fat Products, vol. 1, Fourth Edition (1979), pp. 687-747.
(Continued)

*Primary Examiner* — Vu A Nguyen
(74) *Attorney, Agent, or Firm* — Sutherland Asbill & Brennan LLP

(57) ABSTRACT

Viscoelastic compositions capable of preventing microbial proliferation and capable of capturing microbial membrane and cell wall decomposition products are provided. The compositions comprise thermal reaction products of blends of fatty acids derived and isolated from drying and semi-drying oils such as linseed, safflower, and tung oil, with a polymer component such as for example poly (isobutyl methacrylate). These compositions are capable of capturing microbes and controlling their proliferation at a material on which the compositions are deposited, and further capable of absorption or incorporation of lipopolysaccharide and protein membrane materials and endotoxins.

24 Claims, 8 Drawing Sheets

(51) Int. Cl.

| | | |
|---|---|---|
| *A01N 25/34* | (2006.01) | |
| *A01N 61/00* | (2006.01) | |
| *C02F 1/28* | (2006.01) | |
| *C08F 242/00* | (2006.01) | |
| *C02F 1/50* | (2006.01) | |
| *C02F 1/00* | (2006.01) | |
| *C02F 103/42* | (2006.01) | |

(56) References Cited

U.S. PATENT DOCUMENTS

| | | |
|---|---|---|
| 2,441,068 A | 5/1948 | Hewitt et al. |
| 3,067,154 A | 12/1962 | Sterling |
| 3,755,448 A | 8/1973 | Merianos et al. |
| 3,776,864 A | 12/1973 | Woerner |
| 3,821,109 A | 6/1974 | Gilchrist et al. |
| 3,835,049 A | 9/1974 | King |
| 3,917,528 A | 11/1975 | Orban et al. |
| 3,977,969 A | 8/1976 | Zall |
| 4,156,040 A | 5/1979 | Swider et al. |
| 4,200,561 A | 4/1980 | Chang |
| 4,313,830 A | 2/1982 | Tulin et al. |
| 4,316,730 A | 2/1982 | Eibl |
| 4,420,400 A | 12/1983 | Weitzen |
| 4,420,573 A | 12/1983 | Fogg et al. |
| 4,502,975 A | 3/1985 | Kobayashi et al. |
| 4,519,918 A | 5/1985 | Ericsson et al. |
| 4,786,717 A | 11/1988 | Bretches et al. |
| 4,810,395 A | 3/1989 | Levy et al. |
| 4,964,987 A | 10/1990 | Johnson |
| 5,122,270 A | 6/1992 | Ruger et al. |
| 5,213,689 A | 5/1993 | Kafchinski et al. |
| 5,259,952 A | 11/1993 | Lee |
| 5,326,394 A | 7/1994 | Cobb |
| 5,382,371 A | 1/1995 | Stahl et al. |
| 5,405,932 A | 4/1995 | Bender et al. |
| 5,427,612 A | 6/1995 | Bender |
| 5,429,741 A | 7/1995 | Webb et al. |
| 5,437,793 A | 8/1995 | Alper |
| 5,527,466 A | 6/1996 | Li et al. |
| 5,698,139 A | 12/1997 | Alper |
| 5,746,925 A | 5/1998 | Alper |
| 5,837,146 A | 11/1998 | Alper |
| 5,919,944 A | 7/1999 | Eldin |
| 5,961,823 A | 10/1999 | Alper |
| 6,001,244 A | 12/1999 | Salter et al. |
| 6,168,714 B1 | 1/2001 | Llias et al. |
| 6,180,010 B1 | 1/2001 | Alper |
| 6,337,016 B1 | 1/2002 | Alper |
| 6,475,393 B2 | 11/2002 | Alper |
| 6,491,822 B2 | 12/2002 | Alper |
| 6,623,513 B2 | 9/2003 | Biel |
| 6,805,727 B2 | 10/2004 | Alper |
| 6,883,321 B2 | 4/2005 | Fornof |
| 7,264,721 B2 | 9/2007 | Alper |
| 7,264,722 B2 | 9/2007 | Alper |
| 7,449,119 B2 | 11/2008 | Brown |
| 8,187,459 B2 | 5/2012 | Alper |
| 2001/0042720 A1 | 11/2001 | Alper |
| 2003/0217640 A1 | 11/2003 | Alper |
| 2007/0023357 A1 | 2/2007 | Brown |
| 2010/0249267 A1 | 9/2010 | Jiang et al. |
| 2011/0305895 A1 | 12/2011 | Roth et al. |

FOREIGN PATENT DOCUMENTS

| | | |
|---|---|---|
| WO | 2009/061462 A2 | 5/2009 |
| WO | 2010/089598 A1 | 8/2010 |

OTHER PUBLICATIONS

D. Swern, ed. Bailey's Industrial Oil and Fat Products, vol. 1, Fourth Edition (1979), pp. 687-816.
International Search Report and Written Opinion for PCTIUS2012/042030 mailed Sep. 11, 2012.
International Search Report and Written Opinion for PCTIUS2012/042031 mailed Sep. 20, 2012.
http://www.epa.state.il.us/well-water/common-contaminants.html, retrieved online on Nov. 5, 2014.
Lee, et al., "Culture and Identification of Bacteria from Marine Biofilms," The Journal of Microbiology, 2003, 41(3), pp. 183-188.
PCT International Preliminary Report on Patentability for International Application No. PCT/US2012/042031, issued Dec. 17, 2013.
Poli, et al., "Bacterial Exopolysaccharides from Extreme Marine Habitats: Production, Characterization and Biological Activities," Marine Drugs, 2010, 8, pp. 1779-1802.

ADVANCED VISCOELASTIC ANTIMICROBIAL COMPOSITIONS AND METHODS

CROSS REFERENCE TO RELATED APPLICATIONS

This application is a continuation-in-part of co-pending U.S. application Ser. No. 13/494,410, filed Jun. 12, 2012, and a continuation-in-part of co-pending U.S. application Ser. No. 13/494,386, filed Jun. 12, 2012, both of which claim the benefit of U.S. Provisional Application No. 61/520,646, filed on Jun. 13, 2011, both of which are incorporated herein by reference in their entireties.

TECHNICAL FIELD

This disclosure relates to compositions and methods for capturing microbes such as bacteria and algae, and further relates to methods for controlling microbial proliferation.

BACKGROUND

Certain microbes, for example gram negative bacteria and algae, exude viscoelastic extracellular polymeric substances called exopolysaccharides (EPS) and these exopolysaccharides and their complexes with proteins (exolipoprotien-polysaccharide complexes or EPS/protein complexes) act to protect the microbial cell from external physical and chemical attacks. (Unless otherwise specified, the abbreviation EPS is used herein to refer to EPS materials and EPS/protein complexes collectively.) The EPS also are critical in cellular cohesion responsible for the formation of films, and EPS are involved in adhesion of the microbial cells to surfaces.

EPS materials and EPS/protein complexes are extremely viscoelastic, a feature that can cause unexpected yet severe problems in aqueous environments. For example, the viscoelasticity of less than one pound of brown algae on the total hydroplane surfaces of many naval destroyers is sufficient to reduce top speed from 22 knots to 18 knots and cause fuel consumption to increase by as much as 20%. The presence of these materials in sea water may cause reverse osmosis membranes to lose 20% of their flux within one hour of engagement due to the formation of a monomolecular layer of EPS, which can result in a four-fold increase in the polar component of the surface energy of the membrane.

Also by way of example, dramatic differences in surface energies, contact angles with the polar component water, and surface polarities of clean versus microbial-fouled reverse osmosis membranes have been observed. For example, a comparison of surface energy of clean versus fouled sea water reverse osmosis (SWRO) membranes reveals the following dramatic differences shown in the following table.

TABLE 1

Comparison of Surface Energy of Clean and Fouled
Sea Water Reverse Osmosis (SWRO) Membranes

|  | Contact Angle (deg) with polar component (water) | Surface Energy | Surface Polarity |
|---|---|---|---|
| Clean SWRO | 77.9° | 45.07 | 4.93% |
| Fouled SWRO | 59.3° | 54.87 | 15.94% |

Conventionally, materials such as copper, silver, organic anti-microbial compounds, and other compositions and materials have been employed to prevent microbial growth. While the exact mechanisms by which these materials operate often are not understood, some compositions such as organic bactericides function primarily by interfering with cell wall formation. The interference with cellular metabolism and respiration is implicated in other materials, such as the metals. In effect, all of these conventional materials act in some manner as poisons, which also may impart adverse effects on human health and ecology. Therefore, coatings treated with these materials and their direct introduction into water is generally undesirable due to their negative effects on flora, fauna, and humans.

In order for microbes to reproduce and anchor to a surface, they must first exude an EPS "nest" which causes divided cells to cohere to each other, and provides the necessary conditions for them to anchor to a substrate. This EPS nest is critical to cell survival, and without such a structure, cells generally will wither and die. However, conventional antimicrobial treatments that produce dead cells also can be problematic because of the adverse effects of cell membrane decomposition products, for example the components of the cell walls of certain dead bacteria. These membrane decomposition products are known as endotoxins, and endotoxins can cause human diseases through inhalation of aerosols containing these materials, through ingestion, and through skin contact. Moreover, endotoxins may be one of the sources of EPS materials responsible for fouling filtration surfaces such as in membrane filtration devices and in anti-bacterial filters.

There are also adverse effects to water treatment and purification devices which arise from the presence of microbes and their decomposition products in water, and which are problematic to human health. For example, water purification devices often experience what is referred to microbial "grow-through". Media filters, sand filters, carbon filters, clay filters, and others have limited life spans due to the growth of bacteria. As a result, these materials become septic and malodorous and release cellular decomposition products as part of their effluent. These decomposition products, in turn, foul and interfere with the efficient operation of downstream treatment technologies such as membrane filtration and ion exchange systems. Therefore, the presence of cellular decomposition products in water can cause human health concerns through various routes of entry. Although poisons such as silver and bactericides may kill microbes, they do nothing to address the microbial decomposition products, and their use can in some cases actually enhance the pathogenicity of the water.

Therefore, what are needed are non-toxic compositions and methods that provide antimicrobial activity, which can address the need for safer and more environmentally benign ways to protect various substrates, media, and surfaces from microbial growth and proliferation. One possible approach would be to develop ways that could help prevent the EPS from fulfilling its role in cellular organization and cohesion. It would be desirable if the non-toxic compositions and methods could not simply exhibit antimicrobial activity, but also address the problems from endotoxins that may arise from that antimicrobial activity. Desirably, these materials would not result in negative effects on flora, fauna, and humans.

SUMMARY

Now in accordance with the present invention, a method has been found for producing a new and unexpectedly improved compositions useful in controlling microbial proliferation at a material in contact with a fluid that contains microbes, and which further remove microbes and endotoxins from the fluid, such as water, air, and other benign gases. Specifically, this disclosure provides a method for controlling microbial proliferation at a material which during use is contacted with a microbe-containing fluid, whereby the microbes are deposited at portions of the material, the method comprising:

(a) providing an initial glyceride composition comprising one or more drying oils and/or semi-drying oils;

(b) cleaving and separating fatty acids from the initial glyceride composition to provide a blend comprising saturated, mono-unsaturated, and/or poly-unsaturated fatty acids, the fatty acid blend being unique to the initial glyceride composition;

(c) thermally reacting the fatty acid blend from step (b) with a methacrylate or acrylate polymer compound to yield a homogeneous thermal reaction product as a proliferation controlling composition;

(d) coating at least a portion of the material which during use is contacted with the microbe-containing fluid with the proliferation controlling composition; and (e) contacting the coated material with the fluid in which the microbes are contained.

Reference is made to the present inventor's U.S. Pat. Nos. 5,437,793; 5,698,139; 5,837,146; 5,961,823; 6,180,010; 6,475,393; and 6,805,727 (all of which are incorporated herein by reference in their entireties), which disclose compositions having extremely strong affinities for oil and hydrocarbon contaminants in fluids such as water. These prior art absorption compositions (referred to herein as the "PAAC(s)") can be used, for example, by passing fluid streams containing the noxious contaminants through filtration media incorporating the PAACs, by which the contaminants are immobilized at the media. The PAACs generally comprise a homogeneous thermal reaction product of an first reactant selected from the group consisting of fatty acid esters, glycerides, alkenes and alkynes, and a second reactant such as a methacrylate or acrylate polymer component. In most cases, the thermal reaction products employed as the first reactant the aforementioned fatty acid esters by direct use of a drying oil such as linseed oil or tung oil. These prior patents also mention that the reactant could be a fatty acid. However, in the present disclosure, a completely different first reactant is used, with surprising and unexpected results in performance of the resulting product, and indeed in the product itself. The resulting composition exhibited surprising performance for controlling microbial proliferation at a material which during use is contacted with a microbe-containing fluid such as water, air, or benign gases.

Thus in accordance with the present invention, an initial glyceride composition is provided which comprises one or more drying oils and/or semi-drying oils. This composition and/or compound is not, however, used as in the prior art as the first reactant to produce an absorption composition or PAAC. Rather the initial glyceride composition is subjected to a cleaving and separating step to yield a blend comprising the constituent saturated and mono- and poly-unsaturated fatty acids, the fatty acid blend being unique to the initial glyceride composition. It is this unique fatty acid blend which is then thermally reacted with a methacrylate or acrylate polymer compound to yield a homogeneous thermal reaction product having coagulation and viscoelastic rheology modification properties. The thermal reaction product is found to itself be a uniquely distinct composition, which possesses considerably enhanced characteristics and effectiveness when employed in uses including those with which the PAACs have heretofore been used.

According to one aspect of this disclosure, the initial glyceride composition that is subjected to a cleaving and separating step to yield a constituent fatty acid blend can be selected from, or can comprise, one or more drying and/or semi-drying oils from any source and having any level of processing, purification, and/or additives, including having no processing, purification and/or additives. For example, and not by way of limitation, the initial glyceride composition that is subjected to a cleaving and separating step to yield a constituent fatty acid blend can be selected from, or alternatively can comprise:

1) an "off-the-shelf" or "OTS" oil, also termed a "commercial" or "purified" oil. The OTS oils typically are natural drying and/or semi-drying oils that have been processed for example by conventional washing, purification, and/or refining steps, and purified to some level to provide a commercial sample. OTS oils also generally include some type of additives such as stabilizers, antioxidants, antiskinning agents (such as methylethyl ketone oxime), rheology modifiers, and/or similar additives.

2) an "unprocessed" oil. An unprocessed oil may be referred to in the art as a "raw" oil, and typically has not been subjected to the conventional washing, purification, and/or refining steps of an OTS oil. However, some level of antioxidants or antiskinning compounds are typically included even in unprocessed oils;

3) A "natural pressed" oil. The term "natural pressed" oil is used herein to reflect a natural oil that has been directly derived from the seed by pressing, but is otherwise unprocessed before its use and absent any additives. Specifically, the natural pressed oil is used without any further purification or washing steps and without the use of any additives such as stabilizers, antioxidants, antiskinning agents (such as methylethyl ketone oxime), rheology modifiers, and the like; and/or 4) any combination thereof.

The initial glyceride composition can be selected from, or can comprise, a drying oil, a semi-drying oil, or a combination thereof. Examples of useful oils include but are not limited to linseed oil, safflower oil, tung oil, soybean oil, menhaden oil, hemp oil, sunflower oil, rapeseed oil, and the like, including mixtures thereof.

In one aspect, natural pressed oils can be useful, for example, in providing a more tailored end product. For example, natural pressed oils can offer more controllable curing or crosslinking by allowing any additives such as curing agents or rheology modifiers to be selected and added if and when desired. The natural pressed oils also can be customized according to the particular source selection for the specific oil, such as the region, climate, or season.

Even though the disclosed compositions are useful in separation of oil and hydrocarbons as such, they are also found to be particularly useful in separation from water and gases of further noxious contaminants, including microbes, endotoxins, triglycerides, and cholesterol. The disclosed compositions are also useful for capturing microbes, and for controlling, reducing or minimizing microbial proliferation, at a material which during use is contacted with a microbe-containing fluid, whereby the microbes are deposited at or on the material, such as a surface.

While the exact mechanism acting to remove these further species is not totally understood, a hypothesis has been developed regarding the nature of the mechanism. Noting that this disclosure to not require any specific mechanism by which the compositions function, and while not intending to be bound by theory, the hypothesis observes that exterior portions of most cells, including algae, plankton, sulfate reducing bacteria and protists, are composed of a cell membrane, the major constituent of which is a lipid bi-layer, encased in the exoplasmic surface of the cell composed of exopolysaccharide/ glycolipid assemblages. The lipid bi-layer is composed of phospholipids which are the diglyceride esters of mono-unsaturated or polyunsaturated fatty acids of glycerin phosphate. This layer almost always contains the essential fatty acids (alpha-linolenic acid and linoleic acid) and usually includes gamma-linolenic acid, and palmitoleic acid (mono-unsaturated). These same fatty acids can be derived or obtained from drying oils and semi-drying oils in the starting form of triglyceride esters from fish (menhaden oil), flaxseed (linseed oil), hemp oil, soy oil, rapeseed, sunflower seed and a great many other oily seeds and from olives.

The exoplasmic surface of the cell is a complex agglomeration of exopolysaccharides ("EPS"). These vary greatly in composition, but they are usually polyanionic due to the presence of uronic acids or ketal linked pyruvate. These polysaccharides yield highly viscous aqueous solutions with viscoelastic properties. Glycolipids are obtained when a carbohydrate chain is bonded to a phospholipid on the exoplasmic surface of the cell. They can exist in the form of glycolipid (sugar bonded directly to the fatty acid) or glycerol-glycolipid (sugar bonded to glycerin of diglyceride fatty acid ester). Glycolipids also always contain essential and other polyunsaturated, mono-unsaturated and saturated fatty acids some of which are identical and others similar to those derived from seed oils yielding drying, semidrying and non-drying oils. The formation of a tertiary structure due to the interaction of the lipids and polysaccharides is known as biofilm formation. This biofilm can occur on the cell and on other surfaces as a result of interactions of living cells or resulting from the decomposition of dead cells. The resultant film is usually viscoelastic and amphiphatic in its water solubility characteristics.

This biofilm is the medium/matrix upon which newly produced cells anchor themselves to a substrate and to each other. Production and propagation of this film through a substrate or filter media in conjunction with cellular reproduction results in the primary mechanism by which cells and microbial matter are able to penetrate, saturate and be discharged through filter media (e.g. non-wovens such as MBPP (melt blown polypropylene)), and granular material such as clay, sand and granular activated carbon) which is initially able to intercept and prevent mechanical penetration and breakthrough of the microbes. This phenomenon, known as grow-through results in penetration and discharge/breakthrough of microbes through filter media which may be sufficiently fine or efficient enough to initially intercept and prevent discharge of microbes and microbial matter through purely physical/mechanical breakthrough. It is theorized that microbes captured by filters infused with the compositions of the invention are unable to anchor on the substrate or to adhere to each other and multiply due to incorporation or denaturing of the EPS (exopolysaccharide) matrix. This denaturing is probably the result of the high affinity of the EPS for the compositions due to their very similar physiochemical properties.

The thermal reaction product(s) of the present disclosure (herein "TRP") is the product (thermally driven self-assembling phase transition product) of fatty acid blends cleaved from triglyceride esters of drying and/or semi drying oils (the same fatty acids as contained in glycosaccharides and phospholipids) and IBMA (isobutyl methacrylate) and n-BMA (n-butyl methacrylate) (similar in properties to EPS). The result is a polymer which can be used as is or can be cured on to surfaces and in which other viscoelastic, film forming (water insoluble or semi-soluble solvents) or coacervate forming (oils) materials are very soluble. Contact of the TRP with these materials results in a cohesive viscoelastic water insoluble mass. Therefore filters and other surfaces infused with TRP have the ability to incorporate and remove from solution oils, EPS, solvents, fatty acids, microorganisms such as cholesterol microbes, and microbial decomposition products (especially endotoxins and film formers) with very little resistance to flow due to the viscoelasticity of the resultant cohesive mass.

In co-pending and related U.S. application Ser. No. 13/494, 386, an unexpected discovery was disclosed that compositions described in the present inventor's prior patents (PAACs) could be used as effective microbial growth inhibition ("MGI") agents. For example, these PAACs could be applied to or coated onto portions of a material where the microbes thereafter deposit as a result of contact with a liquid carrier in which the microbes are dispersed. These PAACs comprised the homogeneous thermal reaction product of an oil component selected from glycerides, fatty acids, alkenes and alkynes, and a methacrylate or acrylate polymer component. These compositions, which may be referred to herein as MGI absorption compositions and the like, are disclosed in U.S. Pat. Nos. 5,437,793; 5,698,139; 5,837,146; 5,961,823; 6,805,727; 6,475,393; and 6,180,010. These patents disclose that these compositions are useful in capturing and immobilizing a wide variety of fluid contaminants such as hydrocarbons, finely suspended particulates and the like.

Accordingly, the present disclosure thus involves the cleavage and separation of the fatty acids from the initial drying oil/semi-drying oil composition, yielding a unique blend of saturated and mono and poly unsaturated fatty acids which are then caused to undergo a thermal reaction with the aforementioned polymer component, yielding a novel complex self-assembled reaction product (a TRP) which is viscoelastic. These compositions have been discovered to be useful for capturing microbes, particularly bacteria and algae, and for inhibiting the proliferation of these microbes. In addition, the subject compositions and methods can also capture microbial membrane and cell wall decomposition products in addition to immobilizing and prevent proliferation of the microbes themselves. Further, this disclosure relates to compositions and methods for capturing microbes such as bacteria and algae, that can function in an aqueous environment to remove and suppress their growth. Interestingly, the compositions of this disclosure also have the ability to exploit and enhance the cohesive tendency of oils, hydrocarbons, and other noxious species, to yield a cohesive viscoelastic mass, such that the TRP can be used in direct coagulation applications, or can be impregnated and cured into a variety of organic and inorganic substrates, which can then serve in filtration uses.

In addition, it has unexpectedly been discovered that the compositions when used as prescribed by the present disclosure can effectively disrupt the growth mechanisms of living bacteria dispersed in a liquid or other fluid carrier. No additional chemical or photochemical components such as oxidants or UV or gamma radiation are necessary for interference of the growth mechanisms of living microbes using the present compositions and methods. Thus, in an aspect, there is provided a method for capturing microbes and controlling microbial proliferation at a material which during use is contacted with a microbe-containing fluid, for example an aqueous fluid, whereby the microbes are deposited at portions of the material, the method comprising:

(a) coating at least a portion of the material which during use is contacted with the microbe-containing aqueous fluid with the proliferation controlling composition obtained according to the following steps:

(i) providing an initial glyceride composition comprising one or more drying oils and/or semi-drying oils;

(ii) cleaving and separating fatty acids from the initial glyceride composition to provide a blend comprising saturated, mono-unsaturated, and/or poly-unsaturated fatty acids, the fatty acid blend being unique to the initial glyceride composition; and (iii) thermally reacting the fatty acid blend from step (b) with a methacrylate or acrylate polymer compound to yield a homogeneous thermal reaction product as a proliferation controlling composition; and (b) contacting the material with the aqueous fluid in which the microbes are contained;

wherein the method can be carried out in the absence of contacting the aqueous fluid with an oxidant.

Therefore in one aspect and while not theory bound, it is thought that the disclosed compositions and methods function in a fundamentally novel way by their extremely high affinity for EPS and other viscoelastic and oleophilic materials. Therefore, the materials are capable of incorporation, capture, or assimilation of this external layer of the microbial cell, which results in cell death by preventing anchoring of the cell to surfaces and cohesion of the cell to other cells. Additionally, the present compositions and methods are able to incorporate and remove cellular decomposition products containing these oleophilic, viscoelastic components, including endotoxins, thereby preventing downstream fouling and decreasing the pathogenicity of water aerosols. It is thought that the compositions are effective due to their viscoelastic and amphiphatic properties, which impart an extremely high cohesive affinity for EPS, resulting in antimicrobial activity.

While not intending to be bound by theory, it is thought that disclosed embodiment can function by incorporating the microbial-exuded EPS "nest" and preventing the cells from anchoring, which causes them to wither and die. The MGI absorption compositions, for example when diffused on a surface, can capture cells and render them unable to multiply due to incorporation of the exopolysaccharide biofilm matrix which the multiplying cell must exude in order for the new cell to anchor and protect itself. For example, disclosed embodiments provide methods and compositions capable of preventing microbial growth on filter substrates and other surfaces, and of capturing the decomposition products of microbial membranes and cell walls by incorporation of the viscoelastic components into the MGI absorption composition-treated substrate.

The present disclosure also provides embodiments that are able to prevent microbial growth without employing poisons or oxidants, by cohesive incorporation and capture of the EPS which is critical to cell survival. This property enables substances which have been treated with the composition to capture and incorporate cell membrane decomposition products from dead cells. These membrane decomposition products are known as endotoxins, and are known to cause human diseases through inhalation of aerosols containing these materials, through ingestion and through skin contact.

DETAILED DESCRIPTION

Figure 1:
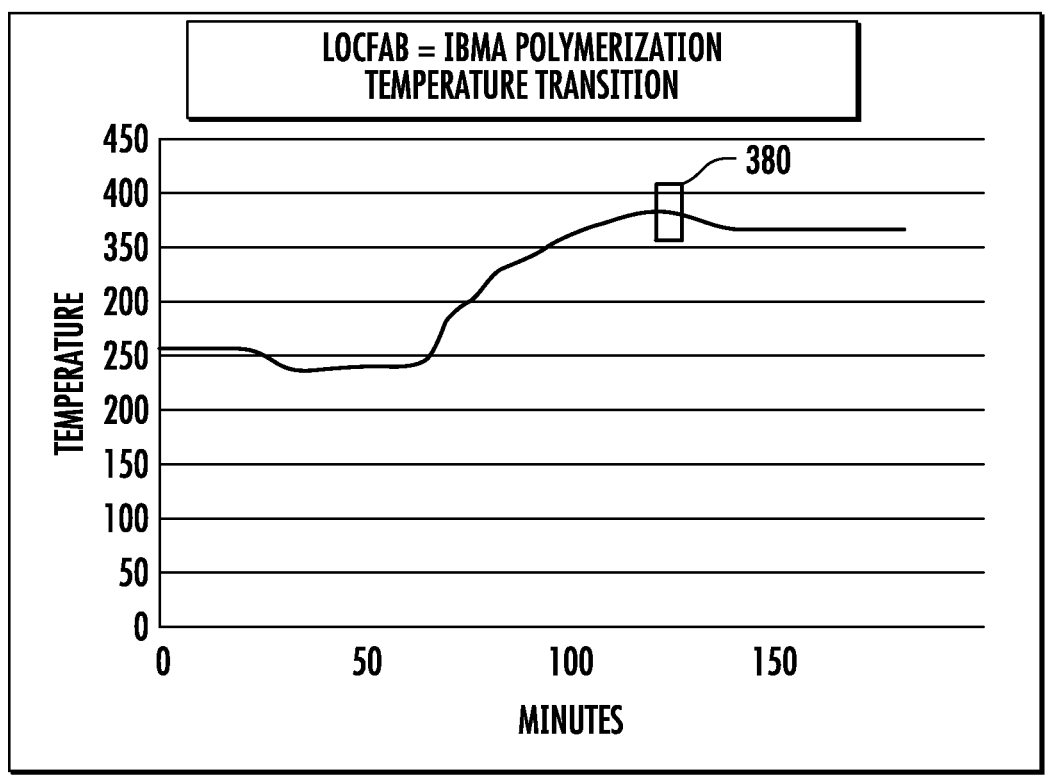
FIG. 1 is a plot of temperature vs. time during synthesis of the thermal reaction product of a linseed oil constituent fatty acid blend (LOCFAB) with an isobutyl methacrylate polymer (IBMA) in accordance with the present invention.
Figure 2:
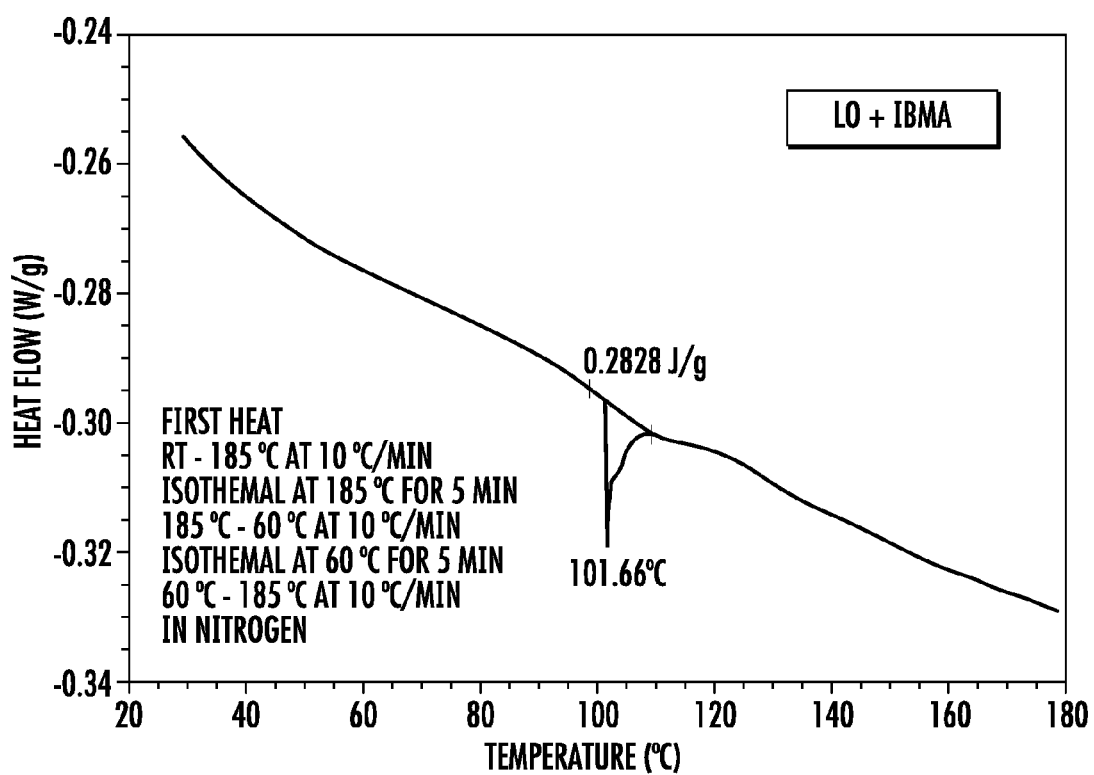
FIG. 2 is a plot yielded where Differential Scanning Calorimetry (DSC) was performed on the reaction products from the thermal reaction of linseed oil (LO) with an isobutyl methacrylate polymer (IBMA).
Figure 3:
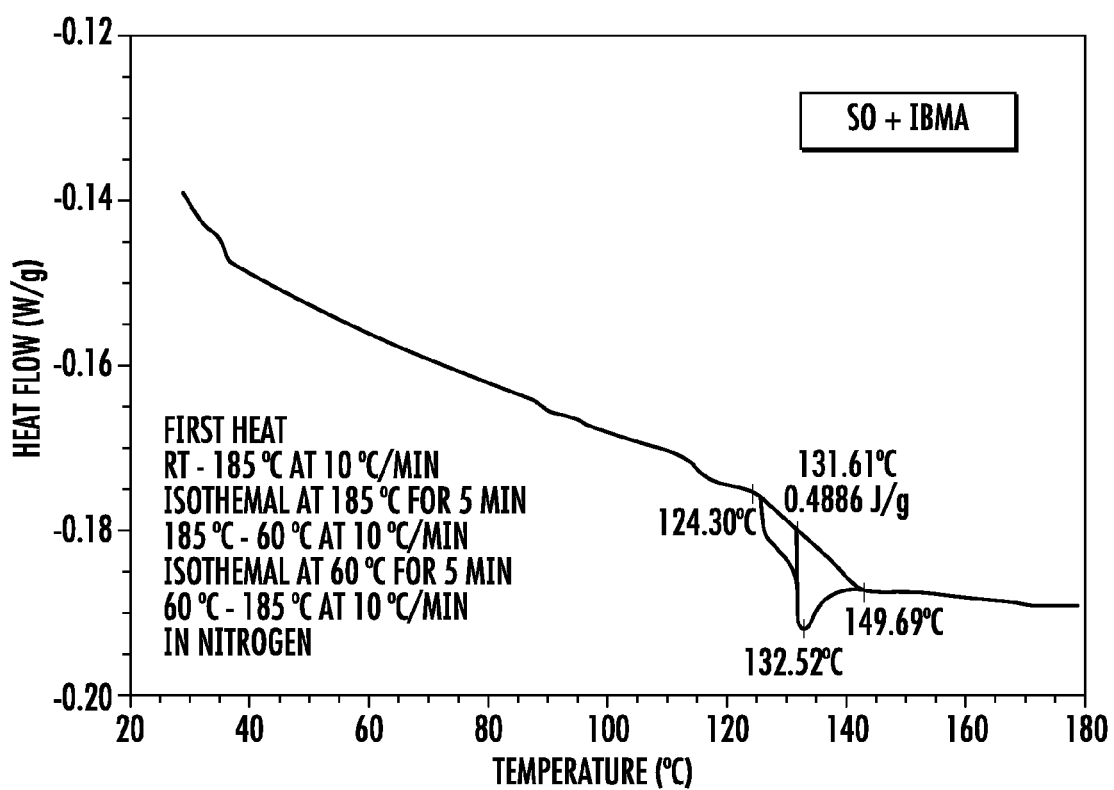
FIG. 3 is a plot yielded where Differential Scanning Calorimetry was performed on the reaction products from the thermal reaction of safflower (SO) with an isobutyl methacrylate polymer (IBMA).
Figure 4:
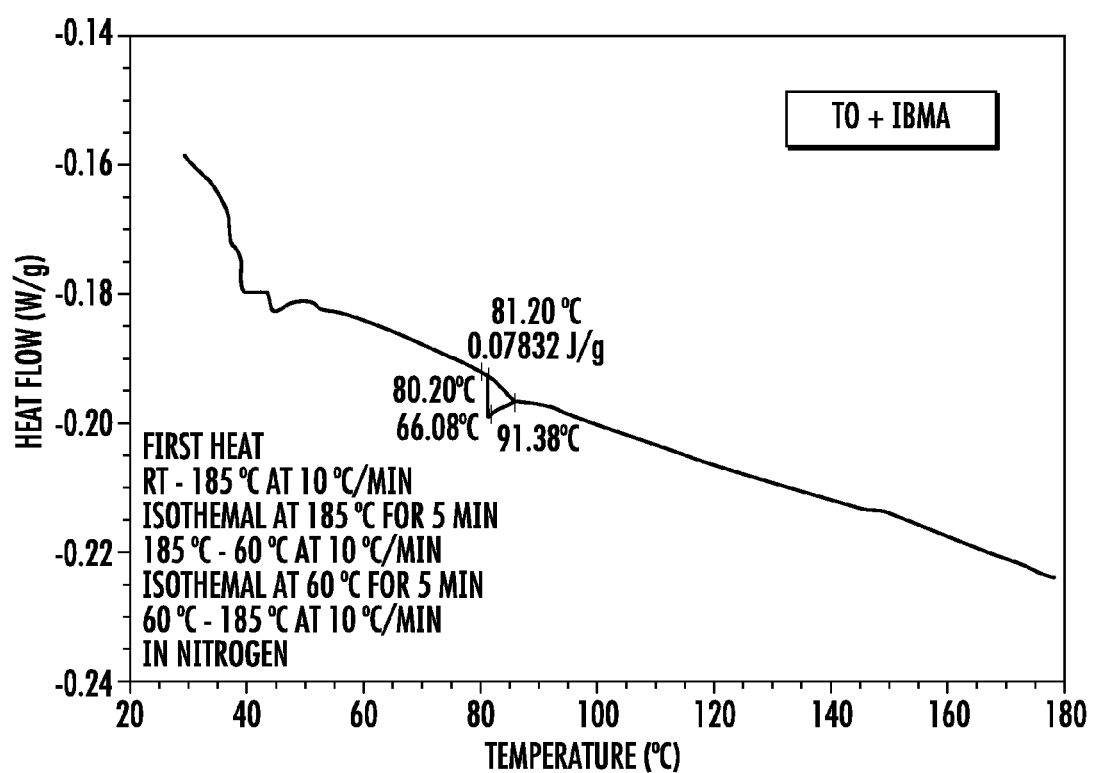
FIG. 4 is a plot yielded where Differential Scanning Calorimetry was performed on the reaction products from the thermal reaction of tung oil (TO) with an isobutyl methacrylate polymer (IBMA).
Figure 5:
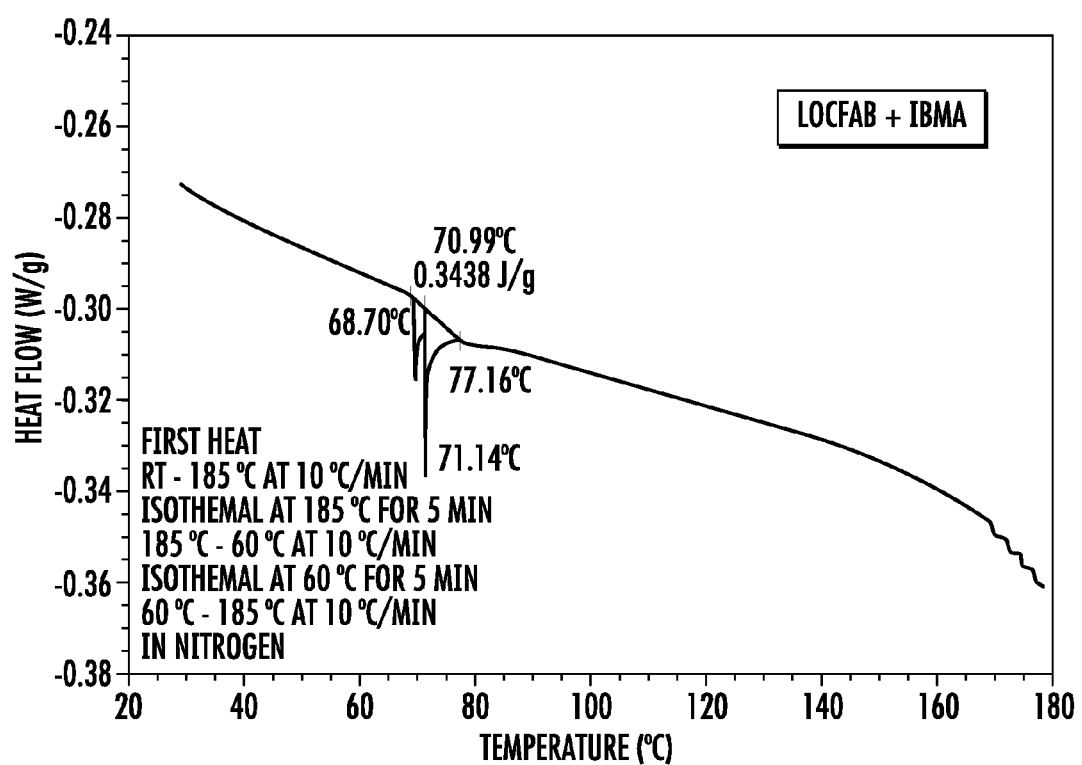
FIG. 5 is a plot yielded where Differential Scanning Calorimetry was performed on the reaction products from the thermal reaction of linseed oil constituent fatty acid blend (LOCFAB) with an isobutyl methacrylate polymer (IBMA).
Figure 6:
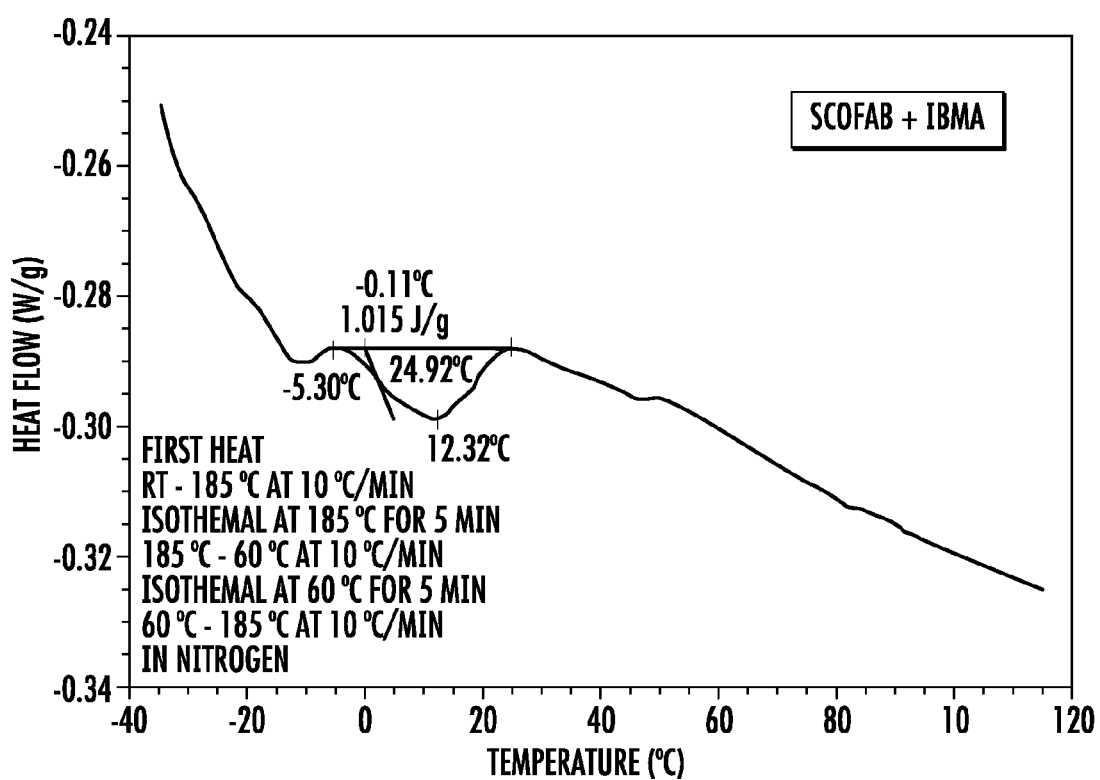
FIG. 6 is a plot yielded where Differential Scanning Calorimetry was performed on the reaction products from the thermal reaction of safflower oil constituent fatty acid blend (SOCFAB) with an isobutyl methacrylate polymer (IBMA).
Figure 7:
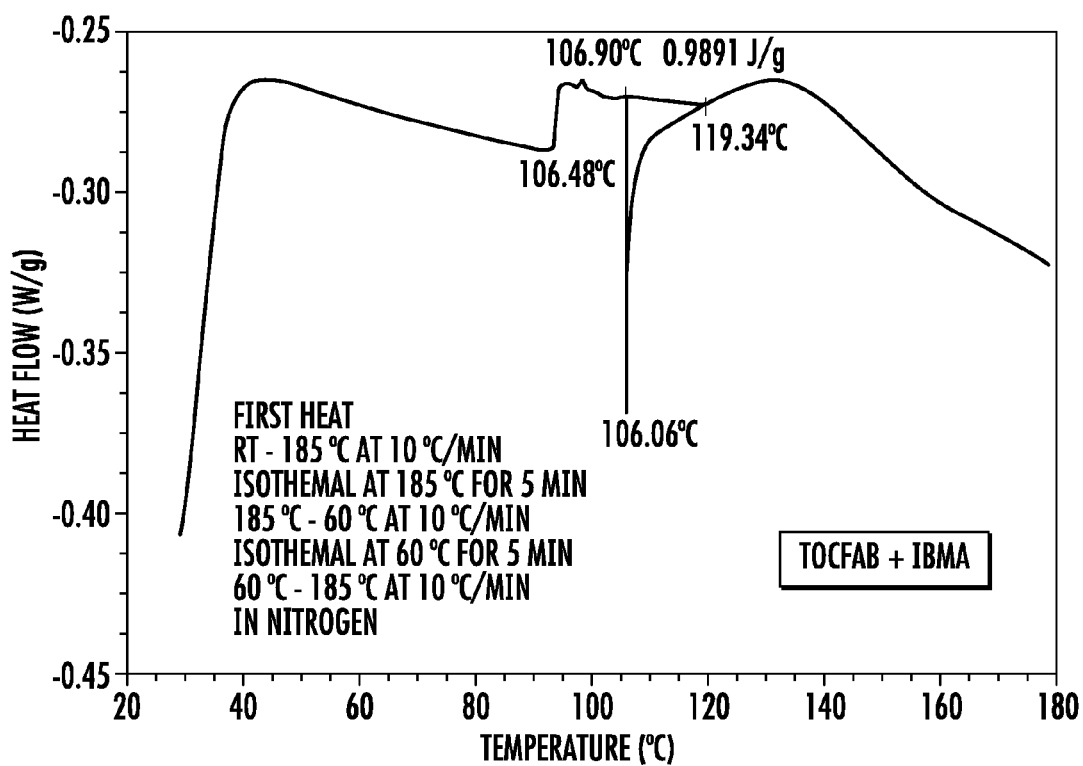
FIG. 7 is a plot yielded where Differential Scanning Calorimetry was performed on the reaction products from the thermal reaction of tung oil constituent fatty acid blend (TOCFAB) with an isobutyl methacrylate polymer (IBMA).

The present disclosure thus provides for the cleavage and separation of the fatty acids from the initial drying oil/semi-drying oil composition, yielding a unique blend of saturated and mono and poly unsaturated fatty acids which are then caused to undergo a thermal reaction with the aforementioned polymer component, yielding a novel complex self-assembled reaction product (a TRP) which is viscoelastic and has the ability to exploit and enhance the cohesive tendency of oils, hydrocarbons, and other noxious species, based on complex pi-orbital interactions to yield a cohesive viscoelastic mass. The TRP is then typically used by impregnating and curing into a variety of substrates. For example, in one aspect, there is provided a method for controlling or suppressing microbial growth and proliferation, the method comprising: providing a material on which microbes deposit; and applying to the portions of said material where the microbes are expected to deposit, a proliferation controlling composition that comprises the TRP as disclosed herein. Therefore the TRP is also a microbial proliferation controlling composition or can be included as a component in a proliferation controlling composition. Upon contact of the coated material with the fluid in which the microbes are contained, microbial growth and proliferation are controlled and suppressed.

In the present process, an initial glyceride composition is provided which comprises one or more drying oils and/or semi-drying oils. The drying oils used are preferably those having an Iodine Number greater than 130, and the semi-drying oils as having an Iodine Number in the range of 115 to 130. In one aspect, the initial glyceride composition that is subject to cleavage and separation of the unique fatty acid blend, comprises only one or more drying oils, such as linseed oil, safflower oil, tung oil, soybean oil, menhaden oil, hemp oil, sunflower oil, rapeseed oil, and mixtures thereof. However in other aspects and uses, the one or more semi-drying oils may also be incorporated in the initial step of the process, as these semi-drying oils can lend some increased softness or flexibility to the final viscoelastic TRP. In one aspect, the drying and/or semi-drying oils used for the proliferation controlling composition can contain one or more double bonds, in which at least two of the fatty acids contain conjugated double bonds.

This initial glyceride composition is subjected to a cleaving and separating step to yield a blend comprising saturated and mono- and poly-unsaturated fatty acids, the fatty acid blend being unique to the initial glyceride composition. Cleaving of the fatty acids can be effected by saponification of the initial glyceride oil composition, followed by acid neutralization of the resulting soap to free the fatty acids therein. Alternatively, the cleaving of the fatty acids can be effected by hydrolyzing the ester bonds of the corresponding glycerides, freeing the fatty acids together with glycerin, followed by separation of the fatty acid to then comprise the fatty acid blend for the subsequent thermal reaction. The fatty acid blend prepared in this manner is referred to herein as the constituent fatty acid blend ("CFAB"). One aspect of the disclosure provides a fatty acid blend comprising alpha-linolenic acid, gamma-linolenic acid, palmitoleic acid, palmitic acid, linoleic acid, oleic acid, and/or stearic acid.

In embodiments of the proliferation controlling composition, the initial glyceride composition comprising one or more drying oils and/or semi-drying oils can be a glyceride derived from natural oils such as oils of vegetable or animal origin. Of the vegetable oils, drying oils such as sunflower, tung, linseed, and the like; and semi-drying oils, such as soybean and cottonseed oil, have been shown to be useful as the glyceride component of the disclosure. Animal oils, such as, for example, fish oil, tallow and lard can also be used as a glyceride component of the composition if desired. It is anticipated that any drying oil or semi-drying oil will work in the composition. Generally, a drying oil is defined as a spreadable liquid that will react with oxygen to form a comparatively dry film. Optionally, combinations of two or more glycerides can be used as reactants with the polymer to provide useful proliferation controlling compositions.

In embodiments, the oil component of the proliferation controlling composition can be a glyceride derived from a drying oil, such as linseed oil, that can be obtained from Cargill, Inc. as Supreme Linseed Oil, or sunflower oil. Where the oil component of the composition is a fatty acid or alkene or alkyne utilized as the reactant with the polymer, it contains from about 8 to 24 carbon atoms, and preferably from about 10 to 22 carbon atoms. Typical fatty acids include both saturated and unsaturated fatty acids, such as lauric acid [dodecanoic acid], linolenic acid, cis-5-dodecanoic acid, oleic acid, erucic acid [cis-docosanoic acid], 10-undecynoic acid, stearic acid, caprylic acid, caproic acid, capric acid [decanoic acid], palmitic acid, docosanoic acid, myristoleic acid [cis-9-tetradecenoic acid], and linoleic acid. Combinations of fatty acids also can be used. Typical alkenes and alkynes contain at least one and preferably one or two degrees of unsaturation, and from about 8 to 24 carbon atoms, with 10-20 carbon atoms being preferred. Preferred alkenes and alkynes are those such as 1-decene, trans-5-decene, trans-7-tetradecene, 1,13-tetradecadiene, 1-tetradecene, 1-decyne, and 5,7-dodecadiyne.

The isolated and separated blend of fatty acids derived from the foregoing steps is then thermally reacted with a polymer such as for example poly(isobutyl methacrylate), and the reaction mixture can include or not include a solvent such as for example 2,2,4-trimethyl-1,3-pentanediol monoisobutyrate, d-limonene, or aromatic hydrocarbons such as benzene. That is, the step of thermally reacting the fatty acid blend with a methacrylate or acrylate compound can be carried out in the presence of a solvent or in the absence of a solvent. Optionally, the composition can be diluted with a solvent, such as 2,2,4-trimethyl-1,3-pentanediol monoisobutyrate or acetone, and the diluted composition can then be applied to a desired substrate for use as a filtration media or surface as disclosed herein. This thermal reaction product, which facilitates cohesion of oils, hydrocarbons, and other noxious species independent of agitation and temperature, was also discovered to control, minimize, reduce, or suppress microbial growth and proliferation at or on surfaces that are in contact with fluid (for example, water or air) in which the microbes are contained.

The proliferation controlling composition is a product with characteristics different from either of the starting materials or a simple mixture of the two starting materials, thus showing that a new composition is produced by the thermal reaction. Specifically, the disclosed proliferation controlling compositions pass a clear pill test after being heated at the elevated temperatures and do not separate into two parts upon being cooled but, rather form a homogenous, uniphase (single phase) compound.

Thus, among other things, this disclosure provides a method for controlling microbial proliferation at a material which during use is contacted with a microbe-containing fluid, whereby the microbes are deposited at portions of the material, the method comprising:
  (a) providing an initial glyceride composition comprising one or more drying oils and/or semi-drying oils;
  (b) cleaving and separating fatty acids from the initial glyceride composition to provide a blend comprising saturated, mono-unsaturated, and/or poly-unsaturated fatty acids, the fatty acid blend being unique to the initial glyceride composition;
  (c) thermally reacting the fatty acid blend from step (b) with a methacrylate or acrylate polymer compound to yield a homogeneous thermal reaction product as a proliferation controlling composition; and
  (d) coating at least a portion of the material which during use is contacted with the microbe-containing fluid with the proliferation controlling composition When the coated material is contacting with the fluid in which the microbes are contained, microbial growth and proliferation at or on the coated material in contact with the fluid was discovered to be controlled, minimized, reduced, or suppressed.

The polymer component of the present composition can be a synthetic polymer such as polymers derived from methacrylates. In one aspect, the polymer is derived from methyl methacrylate, ethyl methacrylate, isobutyl methacrylate, or n-butyl methacrylate, or may be a copolymer containing a methacrylate polymer. For example, in some embodiments, the polymer is a poly(isobutyl methacrylate) polymer such as that obtainable from ICI Acrylics as ELVACITE™ 2045, or a methacrylate/methacrylic acid copolymer such as ELVACITE™ 2008 or 2043. However, other similar polymers can be used to prepare similar compositions that can be used according to this disclosure. Combinations of polymers can be used to advantage in the preparation of the present compositions.

The thermal reaction product can be delivered through infusion and curing into or onto a porous or non-porous substrate material, such as a filter which can be composed of porous and non-porous silica, paper, and synthetic polymers such as melt blown polypropylene (MBPP), a porous ceramic, a porous metal, a mineral particulate such as sand, clay, zeolite, vermiculite or perlite, or so forth. For example, suitable filtration media are disclosed in detail in the present inventor's U.S. Pat. No. 6,190,010 (which is incorporated herein by reference).

In one aspect, for example, the material can comprise a filtration media which is pervious to the fluid and includes interior interstices, wherein the proliferation controlling composition is infused into the filtration media to coat at least a portion of the interior interstices, in which the deposit of the microbes at the coated interstices occurring when the fluid is passed through the filtration media. Moreover, when the fluid is aqueous, the aqueous fluid can further include endotoxins, which are captured by the proliferation controlling composition when the aqueous fluid is passed through the filtration media. According to some aspects, the aqueous fluid can further include dispersed oil particles, which are coalesced by the proliferation controlling composition when the aqueous fluid is passed through the filtration media. Thus, the proliferation controlling composition can be referred to as an absorption composition for this property of coalescing and capturing dispersed droplets of oil and organic compositions.

When the homogeneous thermal reaction product as a proliferation controlling composition is obtained as described which, it can by coated onto at least a portion of a material which during use is contacted with the microbe-containing fluid, whereby the microbes are deposited at portions of the material. When the coated material is contacting with the microbe-containing fluid, this method and composition disclosed herein control, minimize, reduce, and/or suppress microbial growth and proliferation at or on the coated material. In one aspect, the homogeneous thermal reaction product itself can be the proliferation controlling composition used to contact the surface. In other aspects, the proliferation controlling composition can be dispersed in a coating composition which overlies the surface. For example, such a coating composition can comprise or can be selected from a paint, a varnish, a primer, a stain, a polymeric coating composition, and the like.

In a further aspect, the proliferation controlling composition can be viscoelastic, amphiphatic, and have a hydrophilic-lipophilic balance (HLB) of less than 13. The EPS materials are generally amphiphatic and therefore are not efficiently removed by simply oleophilic materials or substrates which are not also amphiphatic and also exhibit viscoelastic properties like the EPS. Amphiphatic materials and chemicals generally possess both hydrophilic and lipophilic properties. When in water, amphiphatic molecules fold in a manner such that the hydrophilic components of the molecule are external and the oleophilic components are unexposed.

While not intending to be limited by theory, it is thought that the present amphiphatic and viscoelastic compositions work well for the disclosed methods as compared to a simple oleophilic substances for the following reasons. When an amphiphatic molecule comes in contact with an oleophilic substrate such as an EPS, it is thought that the oleophilic part of the EPS dissolves into the oleophilic substrate leaving the hydrophilic component exposed. Thus, the oleophilic substrate is likely unable to remove additional EPS's due to the formation of an insulating monomolecular boundary layer. Because the present compositions are also amphiphatic like the EPS, they can exploit the mutual affinity that like compounds have for each other as well as the viscoelasticity of the EPS. Also in contrast to a surface absorption method, the present compositions and methods incorporate and capture the EPS into a cohesive, oleophilic and viscoelastic mass. Once such a mass is formed, introduction of additional EPS results in its continued incorporation and a larger mass is simply formed. In contrast, once an oleophilic substance has dissolved its limit of oleophilic portion of an EPS, a blinding off occurs with these conventional oleophilic materials, resulting from formation of an insulting boundary layer. Therefore, it is thought that a surface should be oleophilic and viscoelastic in order to capture EPS without fouling or, for example, developing high differential pressures across a filter.

According to a further aspect, the antimicrobial composition can be used with a granular filtration media, such as a granular mineral filtration media. Therefore, while embodiments of this disclosure include filter media that can be impregnated or infused and cured with the reaction product chemistry, various granular media work well with the coated and cured reaction product chemistry disclosed herein. For example, the granular mineral filtration media or granular material can comprise or can be selected from a sand, a clay, a zeolite, a vermiculite, a granular carbon, or a granular activated carbon. In some aspects, the coated (or partially coated) granular materials can initially intercept, capture and prevent mechanical penetration and breakthrough of the microbes. Such treated or coated granular mineral filtration media are also useful for capturing microbes, and for controlling, reducing or minimizing microbial proliferation, at the filtration media, which during use is contacted with a microbe-containing fluid. For example, such devices can be used to treat produced water from oil and gas production, where flow of process water and boiler condensate can be restricted by sulfate-reducing bacteria which are able to grow rapidly in aerobic and anaerobic conditions without the need for sunlight.

Treatment of the selected media with the present proliferation controlling composition allows the media to intercept the microbes based on chemical affinity for the external EPS layer while at the same time, causing cell death due to an elimination of the ability to anchor. Decomposition products that are generated by the media are greatly reduced thereby reducing fouling of downstream processes. If desired, fugitive endotoxins can be treated by downstream polishing filters of the proliferation controlling composition or of the traditional MYCELX® composition disclosed in the inventor's patents that are incorporated by reference. Elimination of the ability of the media to support microbial growth prevents production of endotoxins and EPS and prevents sepsis of downstream processes.

A second use of the current disclosure is the incorporation of this chemistry into paints and coatings to prevent fouling and microbial growth. In this aspect, the incorporation of the present compositions into paints and coatings can prevent fouling and growth of the microbes such as bacteria and algae as disclosed herein, but also can prevent fungal growth and fouling on surfaces when so incorporated.

The present methods and compositions are also applicable to the capture and inhibition of so-called nanomicrobes or nanobacteria, as follows. The science of microbial growth, EPS, and their decomposition products has seen considerable advances recently, such as those by J. Craig Ventner and others who have conducted DNA sequencing of ocean water and other natural water sources. Based on these DNA sequencing experiments, researchers have discovered the existence of between 1 and 10 million new species of bacteria. In many cases, these bacteria have not been visualized due to their extremely small size that places them below the capability of optical microscopy, and also due to the destructive nature of electron microscopy. Some researchers believe that these "nanomicrobes" are not only ubiquitous in water, but also may be responsible for much of the chemistry on earth. Confirmation of the existence of these microbes can explain some phenomena which have been anomalous to date, one example of which follows.

Reverse osmosis membranes experience an almost instantaneous decrease in flux and increase in differential pressure upon exposure to water. For example, if a membrane is employed in recirculation mode to clean 55 gallons of water in a drum, the differential pressure of the membrane will increase by 20% within only one hour. If the same water is then recirculated through a new membrane, the same decrease in flux and increase in pressure is experienced. Spectroscopic analysis for chlorophyll indicates the presence of chlorophyll even after the second challenge, even though it would be expected that fouling factors present on the second membrane would have been removed or at least diminished by treatment of the water by the first membrane.

This observation can be explained by the production of additional fouling factor, in this case EPS and endotoxins, and essentially confirms that nanobacteria are ubiquitous and very difficult to remove even in treated water. The observation also suggests that such nanobateria, EPS and endotoxins probably resist removal by adhesion to surfaces. One explanation for the replenishment of the EPS and the endotoxins initially removed is that reverse osmosis of the water decreases the electrolyte concentration and the osmotic pressure, thus killing some of the microbes. This results in the production of cellular decomposition products in the form of endotoxins. Moreover, EPS may be replenished due to enhanced production by the surviving cells as a means of protecting themselves from the environmental insult generated by electrolyte reduction. This results in increased EPS production by the microbe as this its primary way of protecting itself from external chemical and osomotic challenges.

In contrast to aspects of this disclosure, U.S. Pat. No. 7,449,119 to Brown discloses that traditional MYCELX® composition can be used to remove bacterial endotoxins or other bacterial fragments that are freely present after bacteria have been destroyed by chlorine dioxide, and chlorine dioxide is required in all embodiments of the Brown disclosure. The methods disclosed herein can be carried out in the absence of contacting the liquid media or the bacteria with an oxidant or poisons. Further, it was surprisingly found that the advanced compositions of this disclosure, prepared by cleaving and separating fatty acids from the initial glyceride composition to provide a fatty acid blend unique to the initial glyceride composition, and thermally reacting the fatty acid blend with a methacrylate or acrylate polymer component, provide a thermal reaction product that functions as a microbial proliferation controlling composition. Therefore, the present new compositions are capable of preventing bacterial growth on surfaces or filtration media to which such compositions are applied without oxidants or poisons by cohesive incorporation and capture of the EPS which is critical to cell survival. This feature also enables substances which have been treated with the composition to capture and incorporate endotoxins and other cell membrane decomposition products from dead cells, once they are formed.

The Brown patent also discloses a number of natural or synthetic materials are capable of physically removing endotoxins, including synthetic materials such as polyurethane, polyethylene, polypropylene and other synthetic oleophiles including cross-linked polymers and rubber materials. In contrast to the present disclosure, these materials are not capable of preventing or inhibiting microbial growth, likely because they cannot prevent the EPS from fulfilling its role in cellular organization and cohesion. While not intending to be bound by theory, it is believed that cells captured on a TRP-infused surface comprising the present proliferation controlling composition are unable to multiply due to incorporation of the exopolysaccharide biofilm matrix which the multiplying cell must exude in order for the new cell to anchor itself and to protect the new cell from the environment.

Therefore, in a further aspect, the present disclosure provides a means to address and counter even the persistent replenishment of the EPS and the endotoxins that arise due to enhanced production by the surviving cells from an initial treatment. Conventional treatments do not afford such versatile, targeted methods and compositions that area capable of this functionality. In addition, more conventional or traditional treatments are generally toxic compositions, and do not provide the environmentally safe methods to protect various substrates and surfaces from microbial growth and proliferation. Therefore, the present materials can avoid the negative effects on flora, fauna, and humans, and afford long-term functionality from its continued incorporation of microbes, their EPS, and endotoxins that is so desirable.

The present invention is further illustrated by the following Examples, which are indeed to be considered as merely exemplary and not delimitative of the invention otherwise described.

EXAMPLES

Example 1

Isolation of Linseed Oil Constituent Fatty Acid Blend

A 200 g sample of an unprocessed linseed oil and 38.27 g of potassium hydroxide were charged into a beaker with a magnetic stirrer, heated and stirred continuously at 80-85° C. for about one hour. After the saponification was complete (thickening and formation of visible glycerin layer), the mixture was cooled in water bath and filtered to separate the soap from the glycol. The pH of the soap was around 10. The soap was acidified with concentrated hydrochloric acid to pH 4. Acidification of the soap springs free fatty acid with potassium chloride by product. The fatty acids were separated from the salt by decanting. Samples of the blend of fatty acids were then subjected to GC/MS (gas chromatography/mass spectrometry) and FAME (fatty acid methyl ester) analysis.

For comparative purposes, an off-the-shelf (OTS) purified commercial linseed oil was also subjected to cleavage of the constituent fatty acids as described above, and the resulting fatty acids analyzed to provide comparative data. The off-the-shelf (OTS) purified commercial linseed oil data are shown in Table 2, and the analysis of the fatty acid blend resulting from cleaving the unprocessed linseed oil, to provide the linseed oil constituent fatty acid blend (LOCFAB) yielded the results shown in Table 3 below.

TABLE 2

Content of methyl esters in OTS (purified) commercial linseed oil expressed as fatty acids.

| Component | % of Total |
| --- | --- |
| Palmitic | 22.40 |
| Linoleic | 7.35 |
| Oleic | 53.33 |
| Stearic | 16.92 |
| Total | 100.00% |

TABLE 3

Content of fatty acids in unprocessed linseed oil constituent fatty acid blend (LOCFAB)

| Component | % of Total |
| --- | --- |
| Palmitic | 16.11 |
| Linoleic | 8.33 |
| Oleic | 65.53 |
| Stearic | 12.03 |
| Total | 100.00% |

Among other things, a comparison of the data demonstrates how unprocessed linseed oils (or even natural pressed oils) can be tailored by selecting the oil from specific sources or from seeds grown in specific locations to provide a constituent fatty acid blend with a higher concentration of certain fatty components and a lower concentration of other fatty components. Moreover, and while not intending to be theory bound, it is thought that the naturally-occurring non-glyceride components of the unprocessed linseed oil may assist or complement the unexpected blend of constituent fatty acids in providing the improved results shown in the data of Example 4. That is, the marked difference in the fraction of the same fatty acids respectively in Tables 2 and 3 indicates that the cleavage and separation of a unprocessed linseed oil has yielded an unexpected result.

Example 2

Isolation of Safflower Oil Constituent Fatty Acid Blend

A 200 g sample of a unprocessed safflower oil and 38.27 g of potassium hydroxide were charged into a beaker with a magnetic stirrer, heated and stirred continuously at 80-85° C. for about one hour. After the saponification was complete (thickening and formation of visible glycerin layer), the mixture was cooled in water bath and filtered to separate the soap from the glycol. The pH of the soap was around 10. The soap was acidified with concentrated hydrochloric acid to pH 4. Acidification of the soap springs free fatty acid with potassium chloride by product. The fatty acid was separated from the salt by decanting, and the samples were then subjected to GC/MS (gas chromatography/mass spectrometry) and FAME (fatty acid methyl ester analysis).

For comparative purposes, an off-the-shelf (OTS) purified commercial safflower oil was also subjected to cleavage of the constituent fatty acids as described above, and the resulting fatty acids analyzed to provide comparative data. The off-the-shelf (OTS) purified commercial safflower oil data are shown in Table 4, and the analysis of the fatty acid blend resulting from cleaving the unprocessed safflower oil, to provide the safflower oil constituent fatty acid blend (SOCFAB) yielded the results shown in Table 5 below.

TABLE 4

Content of methyl esters in OTS (purified) commercial safflower oil expressed as fatty acids.

| Component | % of Total |
| --- | --- |
| Palmitic | 10.18 |
| Linoleic | 2.11 |
| Oleic | 82.73 |
| Stearic | 5.34 |
| Total | 100.00% |

TABLE 5

Content of fatty acids in unprocessed safflower oil constituent fatty acid blend (SOCFAB)

| Component | % of Total |
| --- | --- |
| Palmitic | 12.77 |
| Linoleic | 51.70 |
| Oleic | 30.45 |
| Stearic | 5.08 |
| Total | 100.00% |

Among other things, a comparison of the data demonstrates how unprocessed safflower oils (or even natural pressed oils) can be tailored by selecting the oil from specific sources or from seeds grown in specific locations to provide a constituent fatty acid blend with a higher concentration of certain fatty components and a lower concentration of other fatty components. Moreover, and while not intending to be theory bound, it is thought that the naturally-occurring non-glyceride components of the unprocessed linseed oil may assist or complement the unexpected blend of constituent fatty acids in providing the improved results shown in the data of Example 4. That is, the marked difference in the fraction of the same fatty acids respectively in Tables 2 and 3 indicates that the cleavage and separation of a unprocessed safflower oil has yielded an unexpected result.

Example 3

Isolation of Tung Oil Constituent Fatty Acid Blend

A 200 g sample of a unprocessed tung oil and 38.27 g of potassium hydroxide were charged into a beaker with a magnetic stirrer, heated and stirred continuously at 80-85° C. for about one hour. After the saponification was complete (thickening and formation of visible glycerin layer), the mixture was cooled in water bath and filtered to separate the soap from the glycol. The pH of the soap was around 10. The soap was acidified with concentrated hydrochloric acid to pH 4. Acidification of the soap springs free fatty acids with potassium chloride as a byproduct. The fatty acids were separated from the salt by decanting, and the samples were then subjected to GC/MS (gas chromatography/mass spectrometry) and FAME (fatty acid methyl ester) analysis.

For comparative purposes, an off-the-shelf (OTS) purified commercial tung oil was also subjected to cleavage of the constituent fatty acids as described above, and the resulting fatty acids analyzed to provide comparative data. The off-the-shelf (OTS) purified commercial tung oil data are shown in Table 6, and the analysis of the fatty acid blend resulting from cleaving the unprocessed tung oil, to provide the tung oil constituent fatty acid blend (TOCFAB) yielded the results shown in Table 7 below.

TABLE 6

Content of methyl esters in OTS (purified) commercial tung oil expressed as fatty acids.

| Component | % of Total |
| --- | --- |
| Palmitic acid | 2.46% |
| Linoleic acid | 6.10 |
| Oleic acid | 8.87 |
| Stearic acid | 3.07 |
| α-linoleic acid | 79.50 |
| Total (including trace components) | 100.00% |

TABLE 7

Content of fatty acids in unprocessed tung oil constituent fatty acid blend (TOCFAB)

| Component | % of Total |
| --- | --- |
| Palmitic acid | 14.93 |
| Linoleic | 11.54 |
| Oleic | 39.21 |

TABLE 7-continued

Content of fatty acids in unprocessed tung oil constituent fatty acid blend (TOCFAB)

| Component | % of Total |
|---|---|
| Stearic acid | 13.37 |
| α-linolenic | 20.95 |
| Total | 100.00% |

Again, note the comparison of the data that demonstrates how unprocessed tung oils (or even natural pressed oils) can be tailored by selecting the oil from specific sources or from seeds grown in specific locations to provide a constituent fatty acid blend with a higher concentration of certain fatty components and a lower concentration of other fatty components. Moreover, and while not intending to be theory bound, it is thought that the naturally-occurring non-glyceride components of the unprocessed tung oil may assist or complement the unexpected blend of constituent fatty acids in providing the improved results shown in the data of Example 4. That is, the marked difference in the fraction of the same fatty acids respectively in Tables 6 and 7 indicates that the cleavage and separation of a unprocessed tung oil has yielded an unexpected result.

Example 4

Synthesis of Thermal Reaction Product of Isobutyl Methacrylate and Constituent Fatty Acid Blends A 259 g sample of linseed oil constituent fatty acid blend (LOCFAB) was charged to a three neck round bottom flask, equipped with glass agitator, reflux condenser, thermometer and nitrogen purge line and heated with a heating mantle to 250° F. (degrees Fahrenheit) at a rate 3° F. per minute. When the temperature reached 250° F., 95 g of isobutyl methacrylate was added. The mixture was heated until a temperature range 385° F. with temperature readings recorded every 2 minutes. The mixture remained at this temperature even though heating continued (indicating endothermic phase transition) and yielded a clear pill. The heat setting was kept constant. The temperature was monitored every two minutes and a plot was generated of temperature vs. time (FIG. 1).

A major endothermic event occurred at 380° F. where a temperature drop occurred and the temperature ceased to rise indicating a phase transition and the creation of the thermal reaction product. The samples shown in Tables 8 and 9 below were sent to American Polymer Standards Corporation for gel permeation chromatography to determine the molecular weight (Table 8 and Table 9).

TABLE 8

Before Thermal Reaction [A]

| Sample | Mn | Mw | Mz | Mw/Mn |
|---|---|---|---|---|
| LOCFAB | 360 | 420 | 480 | 1.17 |
| LO + IBMA | 1020 | 1160 | 1300 | 1.14 |
| LOCFAB + IBMA | 340 | 400 | 500 | 1.18 |

[A] Note:
All molecular weights are in Daltons

TABLE 9

After Thermal Reaction [A]

| Sample | Mn | Mw | Mz | Mw/Mn |
|---|---|---|---|---|
| LO + IBMA | 56500 | 95800 | 155300 | 1.7 |
| LOCFAB + IBMA | 109100 | 300400 | 648200 | 2.75 |

[A] Note:
All molecular weights are in Daltons

In this specification including Tables 8 and 9, (Mn) is the number average molecular weight, (Mw) is the average molecular weight, and (Mz) is the Z-average molecular weight.

The endothermic event at 380° F. indicates that a phase transition reaction occurred. Comparison in Table 8 of the molecular weights between the LO+IBMA thermal reaction product and the LOCFAB+IBMA thermal reaction product indicates that two different polymers were formed, which were separate and unique from any of the other constituents.

These same thermal reactions as above were performed on each of the following compositions.

LO+IBMA
SO+IBMA
TO+IBMA
LOCFAB+IBMA
SOCFAB+IBMA
TOCFAB+IBMA

The same endothermic phase transition occurred at 380° F. on each indicating the formation of a thermal reaction product. Differential Scanning Calorimetry (DSC) was performed on each of the reaction products (See the plots of DSCs in FIGS. 2 through 7. Each reaction product exhibited a unique phase transition on the DSC as follows.

LO+IBMA—Phase Transition Temperature 101.66° C. (degrees Celsius)
SO+IBMA—Phase Transition Temperature 132.52° C.
TO+IBMA—Phase Transition Temperature 85.98° C.
LOCFAB+IBMA—Phase Transition Temperature 71.14° C.
SOCFAB+IBMA—Phase Transition Temperature 12.37° C.
TOCFAB+IBMA—Phase Transition Temperature 106.05° C.

The different temperatures in the events on the DSC indicate that a novel product was formed in each reaction.

These results demonstrate, among other things, how reactions using a constituent fatty acid blend provides very different polymers and different results from reactions using the same oil that has not been cleaved. As described above, the particular oil can be selected for a specific range of concentrations of the particular constituent fatty acids, and the resulting isolated fatty acid blend can be tailored as desired to adjust the final properties of the polymer. As compared to the molecular weight properties measured before the thermal reaction (Table 8), the molecular weight properties measured after the thermal reaction (Table 9) are unexpectedly higher for the polymer prepared from the constituent fatty acid blends. Moreover, it is thought that use of a constituent fatty acid blend can reduce the variability of the end product, concentrate the desired properties of interest, and allow an unprecedented level of control over the final polymer properties. The higher molecular weights and polydispersities of the polymer derived from the constituent fatty acid blend demonstrate how desirable properties for the final product can be enhanced with the reactant acid constitute is not bound in a glyceride structure.

Example 5

Performance Testing of Reaction Products for Coagulation of Oil

Cellulose based tissue paper was infused with each one of the previously mentioned thermal reaction products and the polymer was caused to cure. The infused tissue paper was shredded into uniform small pieces. Two 400 mL beakers were charged with 200 mL of water and two grams of crude oil. 0.2 Grams of linseed oil (LO)+IBMA treated tissue paper were added to one beaker and 0.2 grams of linseed constituent fatty acids blend (LOCFAB)+IBMA were added to the second beaker. The beakers were agitated with a glass stirring rod causing the oil to form a cohesive mass in conjunction with the treated tissue paper. The coagulated tissue paper oily mass was removed and a solvent extraction was performed on each of the beakers with 20 mL of trichlorotriflouroethane in a separatory funnel. The trichlorotriflouroethane fraction was separated and analyzed on an infrared spectrometer for absorbance. The LO+IBMA sample had a total absorbance of 1344. The LOCFAB+IBMA sample had a total absorbance of 777. The results indicate that the LOCFAB+IBMA was significantly more effective at coagulating the oil than LO+IBMA reaction product.

Example 6

Figure 8:
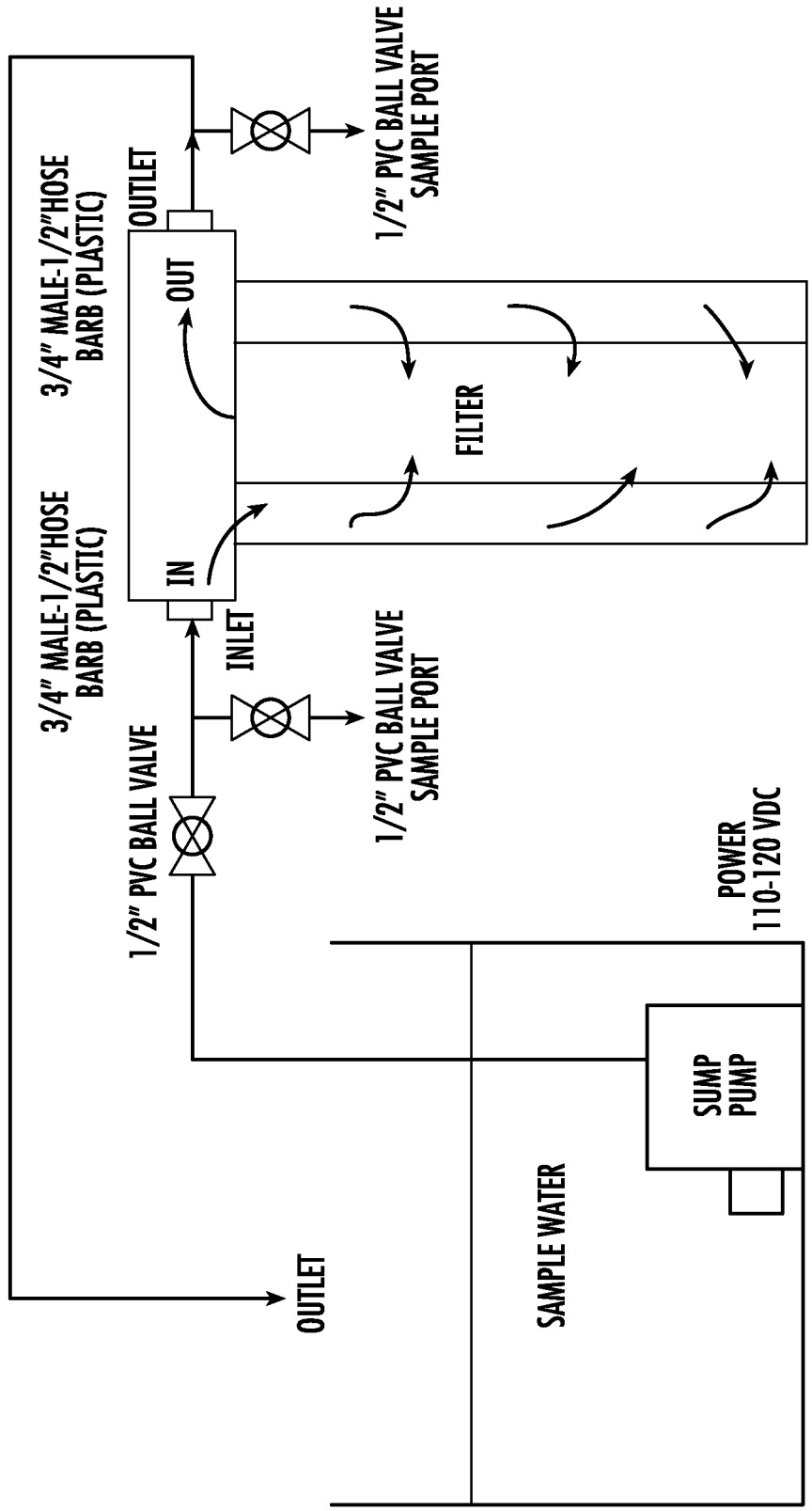
FIG. 8 is a schematic diagram depicting a testing system used to evaluate the performance of products of the invention when used as impregnants in a filtration substrate.

Performance Testing of Reaction Products on Filters for Absorption of Oil 5 inch by 2½ inch sample melt blown polypropylene filters were treated with a 10% composition of the following reaction products:
LO+IBMA
SO+IBMA
LOCFAB+IBMA
SOCFAB+IBMA As illustrated in the schematic diagram of FIG. 8, the filters were engaged in recirculating apparatus with water and crude oil was injected directly into the pump inlet in increments of 20 mL until breakthrough was visible at the outlet. The filters with thermal reaction products with 1 and 2 shown in this example broke through after a total of 180 mL of crude oil. The filters with thermal reaction products 3 and 4 shown in this example did not break through and there remained a visible core of approximately ⅓ of an inch of unconsumed filter material, indicating that reaction products 3 and 4 formed a more cohesive coagulate with the oil.

Example 7

Breakthrough Testing of Reaction Products on Filters with Oil

Two 5 inch by 2½ inch sample melt blown polypropylene filters were treated with a 10% composition of the following thermal reaction products.
LO+IBMA
SO+IBMA
LOCFAB+IBMA
SOCFAB+IBMA The filters (again see FIG. 8) were engaged in recirculating apparatus with four gallon water and crude oil was injected directly into the pump inlet in increments of 20 mL until breakthrough was visible at the outlet. The filters with thermal reaction products 1 and 2 broke through after a total of 180 mL of crude oil. The filters with thermal reaction products 3 and 4 did not break through up to 390 ml of crude oil, indicating that reaction products 3 and 4 formed a more cohesive coagulate with the oil.

Example 8

Microbial Growth Inhibiting Performance on a Filtration Media

The resulting microbial growth inhibiting absorption compositions prepared according the Example 4 are applied to a MBPP (melt blown polypropylene) depth filter and then caused or made to cure by use of heat, actinic radiation, or organic or inorganic polymerization initiators. Such curing methods are provided generally, for example, in U.S. Pat. Nos. 6,180,010; 6,475,393; 6,491,822; and 6,805,727 for the traditional MYCELX® compositions. These microbial growth inhibiting compositions are capable of intercepting bacteria and algae from an aqueous media and preventing their proliferation. These microbial growth inhibiting compositions are also capable of removing bacterial endotoxins from the aqueous media.

Example 9

Microbial Growth Inhibiting Performance on a Granular Media

The resulting microbial growth inhibiting absorption compositions prepared according the Example 4 are applied to sand. The compositions can then be caused or made to cure by use of heat, actinic radiation, or organic or inorganic polymerization initiators. Such curing methods are provided generally, for example, in U.S. Pat. Nos. 6,180,010; 6,475,393; 6,491,822; and 6,805,727 for the traditional MYCELX® compositions. These microbial growth inhibiting compositions are capable of intercepting bacteria and algae from an aqueous media and preventing their proliferation when coating a granular media such as sand. These microbial growth inhibiting compositions are also capable of removing bacterial endotoxins from the aqueous media when coating a granular media such as sand.

Example 10

Microbial Growth Inhibiting Performance on a Nylon Spa Filter

Spa filters are treated with the microbial growth inhibiting absorption compositions prepared according to Example 4. The microbial count is measured for pool water which has been filtered using both nylon spa filters treated with the microbial growth inhibiting absorption compositions disclosed herein, and untreated nylon spa filters, using AOAC method 965.13 [Official Methods of Analysis of the AOAC International]. An approximate four log reduction on microbial count is expected to be observed when using spa filters treated with the microbial growth inhibiting absorption compositions disclosed herein, as compared to the untreated spa filters.

Example 11

Microbial Growth Inhibiting Performance on Filtration Pads and Booms

Melt-blown polypropylene (MBPP) spill response materials are treated with the microbial growth inhibiting absorption compositions prepared according to Example 4 and deployed in a swamp adjacent identical untreated pads and booms. After a three-month deployment, the untreated pads and booms exhibit water-logging and rampant microbial growth. In contrast, the microbial growth inhibiting absorption composition-treated pads and booms remain dry and free of microbial growth.

Example 12

Microbial Growth Inhibiting Performance on Air Filters

The microbial growth inhibiting absorption compositions prepared according to Example 4 are coated and cured into carbon and glass fiber air filters. The resulting filters are deployed in an automotive plant side-by-side with the untreated version of the same carbon and glass fiber air filters. After three months, the untreated filter is expected to be wet and exhibiting the sulfurous smell indicative of microbial growth. In contrast, the microbial growth inhibiting absorption composition-treated carbon and glass fiber air filters are expected to be dry and odor free. A 1-cm coupon could be taken from each filter and placed in an Agar Petri dish and allowed to incubate for 9 days at 27° C. After this incubation period the samples can be inspected and the dish with the untreated coupon will be covered in microbial growth, with the treated coupon expected to exhibit no microbial growth and no odor.

DEFINITIONS

To define more clearly the terms used herein, the following definitions are provided, which are applicable to this disclosure unless otherwise indicated by the disclosure or the context.

The publications discussed or listed in this disclosure are provided solely for their disclosure prior to the filing date of the present application. Nothing herein is to be construed as an admission that the inventor is not entitled to antedate any such published disclosure by virtue of prior invention. If a term used in this disclosure is not specifically defined herein and requires referring to extrinsic sources for construction, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document or portion thereof incorporated herein by reference conflicts with the definition or usage provided herein, the definition or usage provided herein controls.

The term "microbes" as used in this disclosure shall mean those microorganisms that exude viscoelastic exopolysaccharides (EPS), for example, bacteria and algae. Examples of algae that in accordance with the disclosure are subject to capture and growth inhibition include brown algae and green algae. Examples of bacteria that in accordance with the disclosure are subject to capture and growth inhibition include: gram negative bacteria; gram negative sulfate-reducing bacteria; exopolysaccharide-producing cyanobacteria; facultative anaerobic organisms that produce exopolysaccharides; any type of exopolysaccharide-producing marine bacteria; and the like. Additional examples of microorganisms that are subject to such capture and growth inhibition include those disclosed in: Lee et al., "Culture and Identification of Bacteria from Marine Biofilms", *The Journal of Microbiology* 2003, 41(3), 183-188; and Poli et al., "Bacterial Exopolysaccharides from Extreme Marine Habitats: Production, Characterization and Biological Activities", *Marine Drugs* 2010, 8, 1779-1802. In one aspect, fungal species including fungal spores can be excluded from the term microbe.

The term "proliferation controlling composition" is used to describe the homogeneous thermal reaction product, also termed "TRP," which is formed from thermally reacting the fatty acid blend obtained from the initial glyceride composition as described herein, with a methacrylate or acrylate polymer compound.

The term "MYCELX®" or "MYCELX" is used herein to refer to the traditional thermal reaction product composition, specifically, the homogeneous thermal reaction product of an oil component selected from the group consisting of glycerides, fatty acids, alkenes and alkynes, and a methacrylate or acrylate polymer component. Such compositions are described in the present inventor's U.S. Pat. Nos. 5,437,793; 5,698,139; 5,837,146; 5,961,823; 6,180,010; 6,475,393; and 6,805,727.

As used in the specification and the appended claims, the singular forms "a," "an," and "the" include plural referents, unless the context clearly dictates otherwise. Thus, for example, reference to "a methacrylate compound" includes a single methacrylate compound as well as any combination of more than one methacrylate compound if the context indicates or allows, such as multiple methacrylate compounds that are used in combination.

Throughout the specification and claims, the word "comprise" and variations of the word, such as "comprising" and "comprises," means "including but not limited to," and is not intended to exclude, for example, other additives, components, elements, or steps. While compositions and methods are described in terms of "comprising" various components or steps, the compositions and methods can also "consist essentially of" or "consist of" the various components or steps.

Reference throughout this specification to "one embodiment," "an embodiment," or "embodiments" means that a particular feature, structure, or characteristic described in connection with the embodiment is included in at least one embodiment. Thus, the appearances of the phrases "in one embodiment" or "in an embodiment" in various places in the specification are not necessarily all referring to the same embodiment. Furthermore, the particular features, aspects, structures, or characteristics may be combined in any suitable manner in one or more embodiments.

"Optional" or "optionally" means that the subsequently described element, component, step, or circumstance can or cannot occur, and that the description includes instances where the element, component, step, or circumstance occurs and instances where it does not.

Throughout this specification, various publications may be referenced. The disclosures of these publications are hereby incorporated by reference in pertinent part, in order to more fully describe the state of the art to which the disclosed subject matter pertains. The references disclosed are also individually and specifically incorporated by reference herein for the material contained in them that is discussed in the sentence in which the reference is relied upon. To the extent that any definition or usage provided by any document incorporated herein by reference conflicts with the definition or usage applied herein, the definition or usage applied herein controls.

Unless indicated otherwise, when a range of any type is disclosed or claimed, for example a range of the sizes, number, percentages, and the like, it is intended to disclose or claim individually each possible number that such a range could reasonably encompass, including any sub-ranges or combinations of sub-ranges encompassed therein. When describing a range of measurements such as sizes or percentages, every possible number that such a range could reasonably encompass can, for example, refer to values within the range with one significant figure more than is present in the end points of a range, or refer to values within the range with the same number of significant figures as the end point with the most significant figures, as the context indicates or permits. For example, when describing a range of percentages such as from 85% to 95%, it is understood that this disclosure is intended to encompass each of 85%, 86%, 87%, 88%, 89%, 90%, 91%, 92%, 93%, 94%, and 95%, as well as any ranges, sub-ranges, and combinations of sub-ranges encompassed therein. Applicants' intent is that these two methods of describing the range are interchangeable. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means±20% of the stated value, ±15% of the stated value, ±10% of the stated value, ±5% of the stated value, or ±3% of the stated value.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that are employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

Those skilled in the art will readily appreciate that many modifications are possible in the exemplary embodiments disclosed herein without materially departing from the novel teachings and advantages according to this disclosure. Accordingly, all such modifications and equivalents are intended to be included within the scope of this disclosure as defined in the following claims. Therefore, it is to be understood that resort can be had to various other aspects, embodiments, modifications, and equivalents thereof which, after reading the description herein, may suggest themselves to one of ordinary skill in the art without departing from the spirit of the present disclosure or the scope of the appended claims.

What is claimed is:

1. A method for controlling microbial proliferation at a material which during use is contacted with a microbe-containing fluid, whereby the microbes are deposited at portions of the material, the method comprising:
   (a) providing an initial glyceride composition comprising one or more drying oils and/or semi-drying oils;
   (b) cleaving and separating fatty acids from the initial glyceride composition to provide a blend comprising saturated, mono-unsaturated, and/or poly-unsaturated fatty acids, the fatty acid blend being unique to the initial glyceride composition;
   (c) thermally reacting the fatty acid blend from step (b) with a methacrylate or acrylate polymer compound to yield a homogeneous thermal reaction product as a proliferation controlling composition;
   (d) coating at least a portion of the material which during use is contacted with the microbe-containing fluid with the proliferation controlling composition; and
   (e) contacting the coated material with the fluid in which the microbes are contained.

2. A method according to claim 1, wherein the drying and/or semi-drying oils comprise polyunsaturated glyceride esters of fatty acids containing one or more double bonds, in which at least two of the fatty acids contain conjugated double bonds.

3. A method according to claim 1, wherein cleaving the fatty acids is effected by saponification of the initial glyceride composition, followed by acid neutralization of the resulting soap to release the fatty acids.

4. A method according to claim 1, wherein cleaving the fatty acids is effected by hydrolyzing the ester bond of the corresponding glyceride in the initial glyceride composition to release the fatty acids together with glycerin.

5. A method according to claim 1, wherein the starting glyceride composition is selected from one or more of the group consisting of linseed oil, safflower oil, tung oil, soybean oil, menhaden oil, hemp oil, sunflower oil, and rapeseed oil.

6. A method according to claim 1, wherein the drying oils have an Iodine Number greater than 130, and the semi-drying oils have an Iodine Number in the range of 115 to 130.

7. A method according to claim 1, wherein the fatty acid blend comprises alpha-linolenic acid, gamma-linolenic acid, palmitoleic acid, palmitic acid, linoleic acid, oleic acid, and/or stearic acid.

8. A method according to claim 1, wherein the methacrylate or acrylate compound comprises isobutyl methacrylate or n-butyl methacrylate.

9. A method according to claim 1, wherein step (c) of thermally reacting the fatty acid blend with a methacrylate or acrylate compound is carried out in the presence of a solvent.

10. A method according to claim 1, wherein step (c) of thermally reacting the fatty acid blend with a methacrylate or acrylate compound is carried out in the absence of a solvent.

11. A method according to claim 1, wherein the proliferation controlling composition is viscoelastic, amphiphatic, and has a hydrophilic-lipophilic balance (HLB) of less than 13.

12. A method according to claim 1, wherein the material comprises a filtration media which is pervious to the fluid and includes interior interstices, and wherein the proliferation controlling composition is infused into the filtration media to coat at least a portion of the interior interstices, the deposit of the microbes at the coated interstices occurring when the fluid is passed through the filtration media.

13. A method according to claim 12, wherein the fluid is aqueous and further includes endotoxins, which are captured by the proliferation controlling composition when the aqueous fluid is passed through the filtration media.

14. A method according to claim 1, wherein the fluid is aqueous.

15. A method according to claim 14, wherein the aqueous fluid further includes dispersed oil particles, which are coalesced by the proliferation controlling composition when the aqueous fluid is passed through the filtration media.

16. A method according to claim 14, wherein the material comprises a surface which in use is contacted by the fluid, and wherein the proliferation controlling composition is dispersed in a coating composition which overlies the surface.

17. A method according to claim 16, wherein the coating composition comprises a paint.

18. A method according to claim 16, wherein the material comprises a granular mineral filtration media.

19. A method according to claim 16, wherein the material comprises a granular mineral filtration media, and the granular mineral comprises a sand, a clay, a zeolite, a vermiculite, or a granular carbon.

20. A method according to claim 1, wherein the fluid is gaseous.

21. A method according to claim 1, wherein the initial glyceride composition comprises one or more unprocessed or natural pressed drying oils and/or semi-drying oils.

22. A method according to any one of claims 1-21, wherein the method is carried out in the absence of contacting the fluid with an oxidant.

23. A method for capturing microbes at a material which during use is contacted with a microbe-containing aqueous fluid, whereby the microbes are deposited at portions of the material, the method comprising:

(a) coating at least a portion of the material which during use is contacted with the microbe-containing aqueous fluid with a microbe proliferation controlling composition obtained by the steps of:

(i) providing an initial glyceride composition comprising one or more drying oils and/or semi-drying oils;

(ii) cleaving and separating fatty acids from the initial glyceride composition to provide a blend comprising saturated, mono-unsaturated, and/or poly-unsaturated fatty acids, the fatty acid blend being unique to the initial glyceride composition;

(iii) thermally reacting the fatty acid blend from step (a)(ii) with a methacrylate or acrylate polymer compound to yield a homogeneous thermal reaction product as a microbe proliferation controlling composition;

and (b) contacting the material with the aqueous fluid in which the microbes are contained;

wherein the method is carried out in the absence of contacting the aqueous fluid with an oxidant.

24. A method according to claim 23, wherein the proliferation controlling composition is a component of a paint composition that is coated onto at least a portion of the material.

* * * * *